United States Patent [19]

Kennedy et al.

[11] 4,170,145

[45] Oct. 9, 1979

[54] MECHANIZED SCANNING, DISPLAY AND RECORDING ULTRASONIC WELD INSPECTION SYSTEM

[75] Inventors: James C. Kennedy; Wayne E. Woodmansee, both of Seattle, Wash.

[73] Assignee: The Boeing Company, Seattle, Wash.

[21] Appl. No.: 772,481

[22] Filed: Feb. 28, 1977

[51] Int. Cl.² ............................................. G01N 29/04
[52] U.S. Cl. ..................................... 73/620; 73/624
[58] Field of Search ................... 73/67.8 S, 67.9, 67.7, 73/71.5 (U.S. only), 618, 619, 620, 627, 629, 632, 633, 634; 324/37

[56] References Cited

U.S. PATENT DOCUMENTS

| | | | |
|---|---|---|---|
| 3,086,390 | 4/1963 | Brown | 73/67.8 S |
| 3,135,109 | 6/1964 | Werner | 73/67.8 S |
| 3,178,933 | 4/1965 | Bloch et al. | 73/620 |
| 3,323,354 | 6/1967 | Daubresse et al. | 73/67.8 S |
| 3,431,440 | 3/1969 | Osgood | 73/71.5 US |
| 3,537,300 | 11/1970 | Rapuzzi | 73/67.8 S |
| 3,555,888 | 1/1971 | Brown | 73/67.8 S |
| 3,678,736 | 7/1972 | May | 73/67.8 S |
| 3,693,414 | 9/1972 | Soldner | 73/67.8 S |
| 3,721,312 | 3/1973 | St. John | 73/67.8 S |
| 3,722,263 | 3/1973 | Hautaniemi et al. | 73/67.8 S |
| 3,765,229 | 10/1963 | Spencer et al. | 73/67.8 S |

FOREIGN PATENT DOCUMENTS 1600873 9/1970 France ................................. 73/67.8 S

*Primary Examiner*—Stephen A. Kreitman

*Attorney, Agent, or Firm*—Christensen, O'Connor, Johnson & Kindness

[57] ABSTRACT

A scanning mechanism for oscillating a watercoupled ultrasonic transducer, over the surface of a part containing a strip weld and, positioning the ultrasonic transducer along orthogonal paths of travel (one parallel to and the other orthogonal to the strip weld) is disclosed. Position sensors forming part of the scanning mechanism continuously provide signals relating to the orthogonal and oscillatory position of the transducer. An ultrasonic beam emitted by the transducer enters the part and is reflected back and forth between the surfaces of the part, through the weld. Ultrasonic specular reflections (flaw echoes) created by flaws or faults in the weld travel back to the transducer. The "flaw echo" presence and position signals are applied to a monitor subsystem that simultaneously displays the position of the origin of flaw echoes, (and thus flaws), in two planes—one plane lying parallel to the reflecting surfaces of the part, and the other lying orthogonal to the reflecting surfaces and parallel to the strip weld. Preferably, the flaw displays are shaded in accordance with the magnitude of the received flaw echo signals. Further, a video recorder records the data being displayed for subsequent redisplay and analysis. The axis of oscillation of the transducer may coincide with the point where the ultrasonic beam enters the part, or it may lie on either side of the entry point. As an alternative arrangement, two transducers, one for transmission and the other for reception, are used to sense specular reflections that do not return to the transmitting transducer.

26 Claims, 12 Drawing Figures

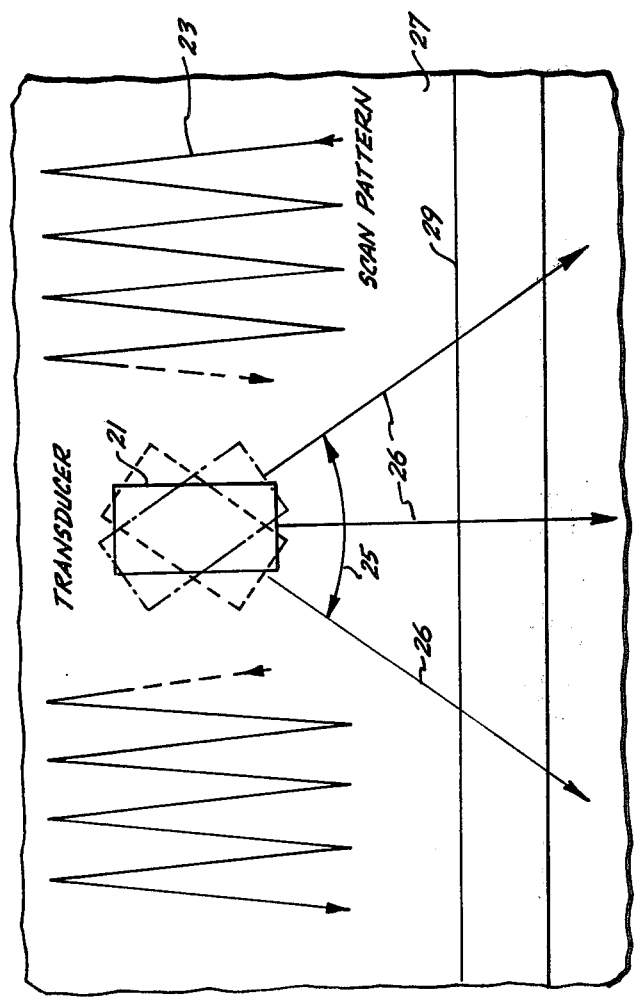
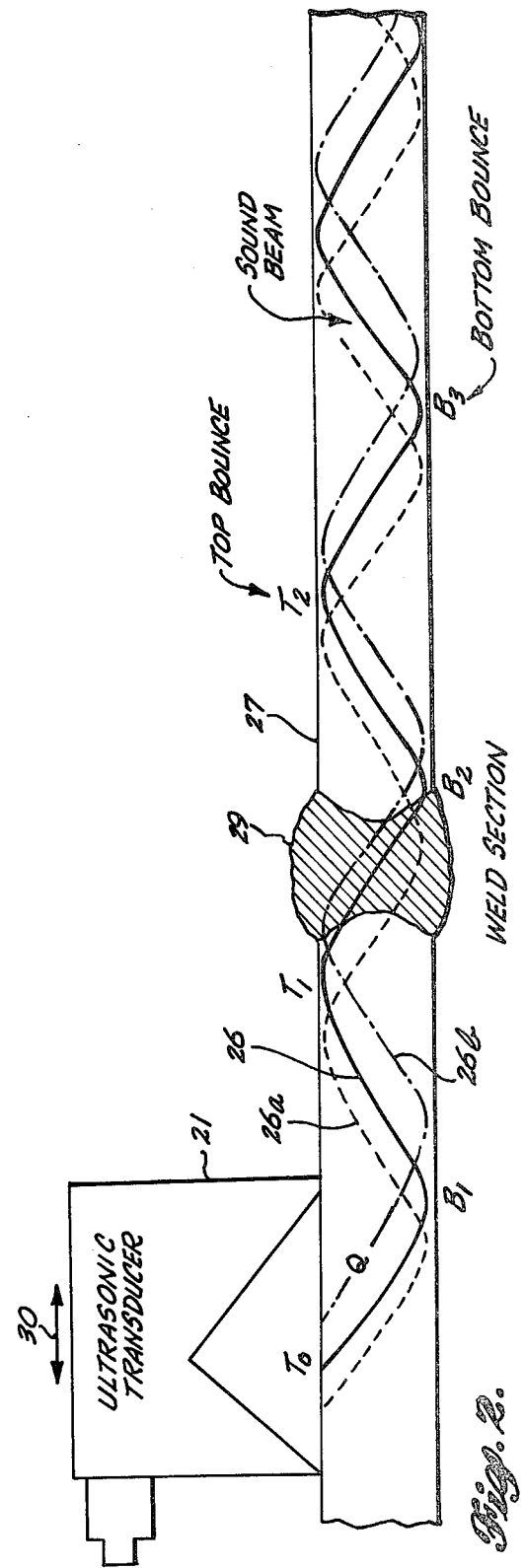

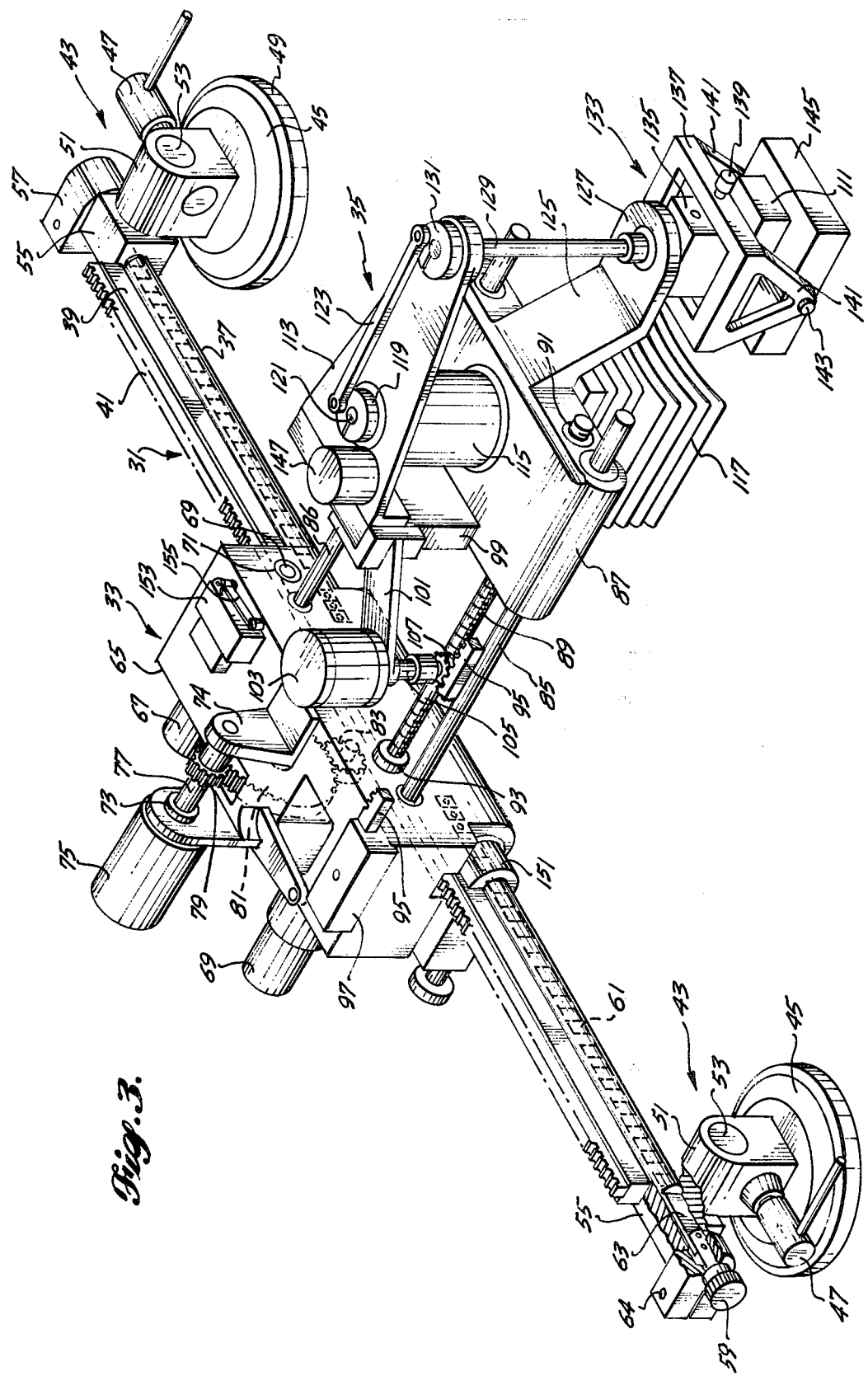

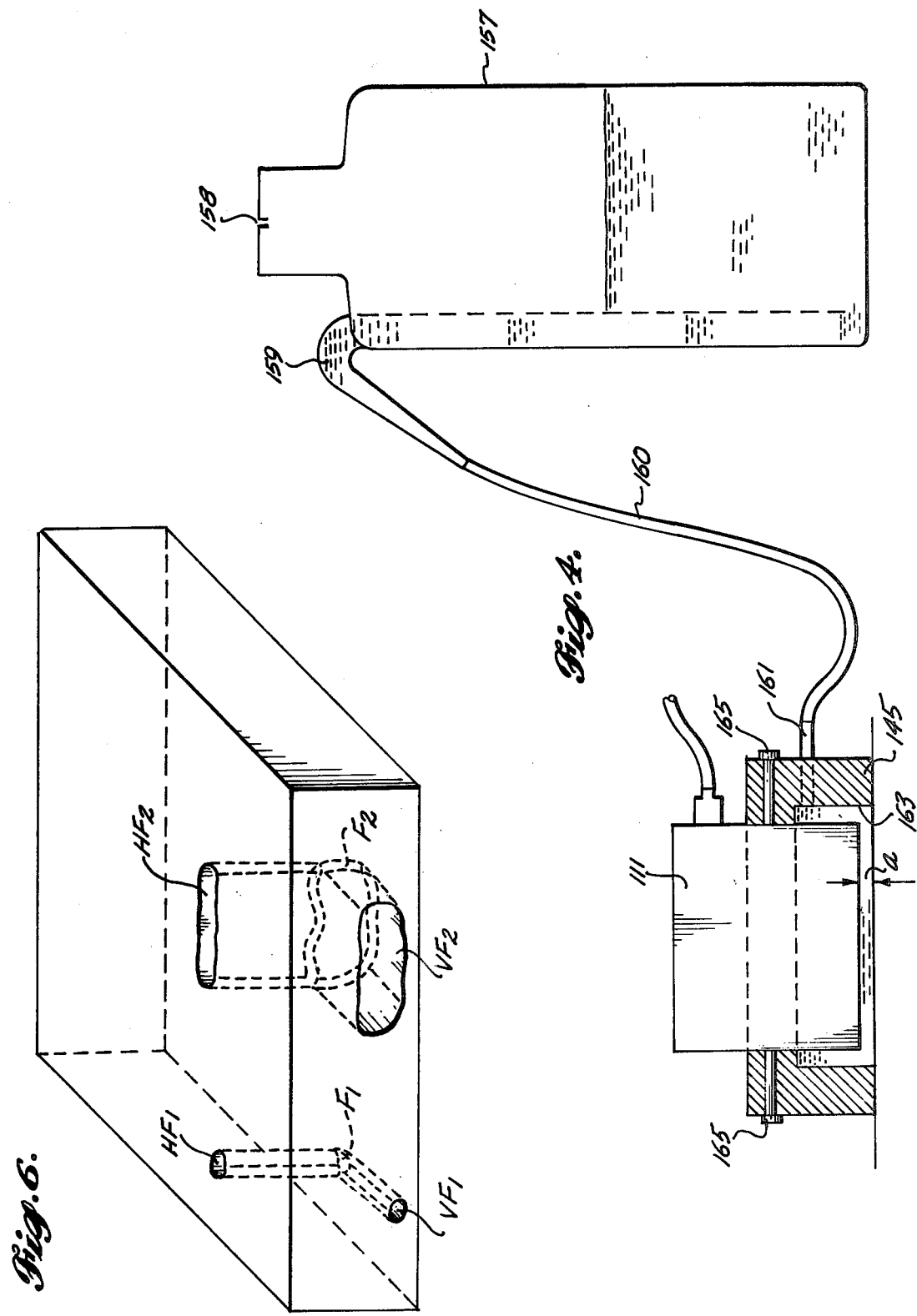

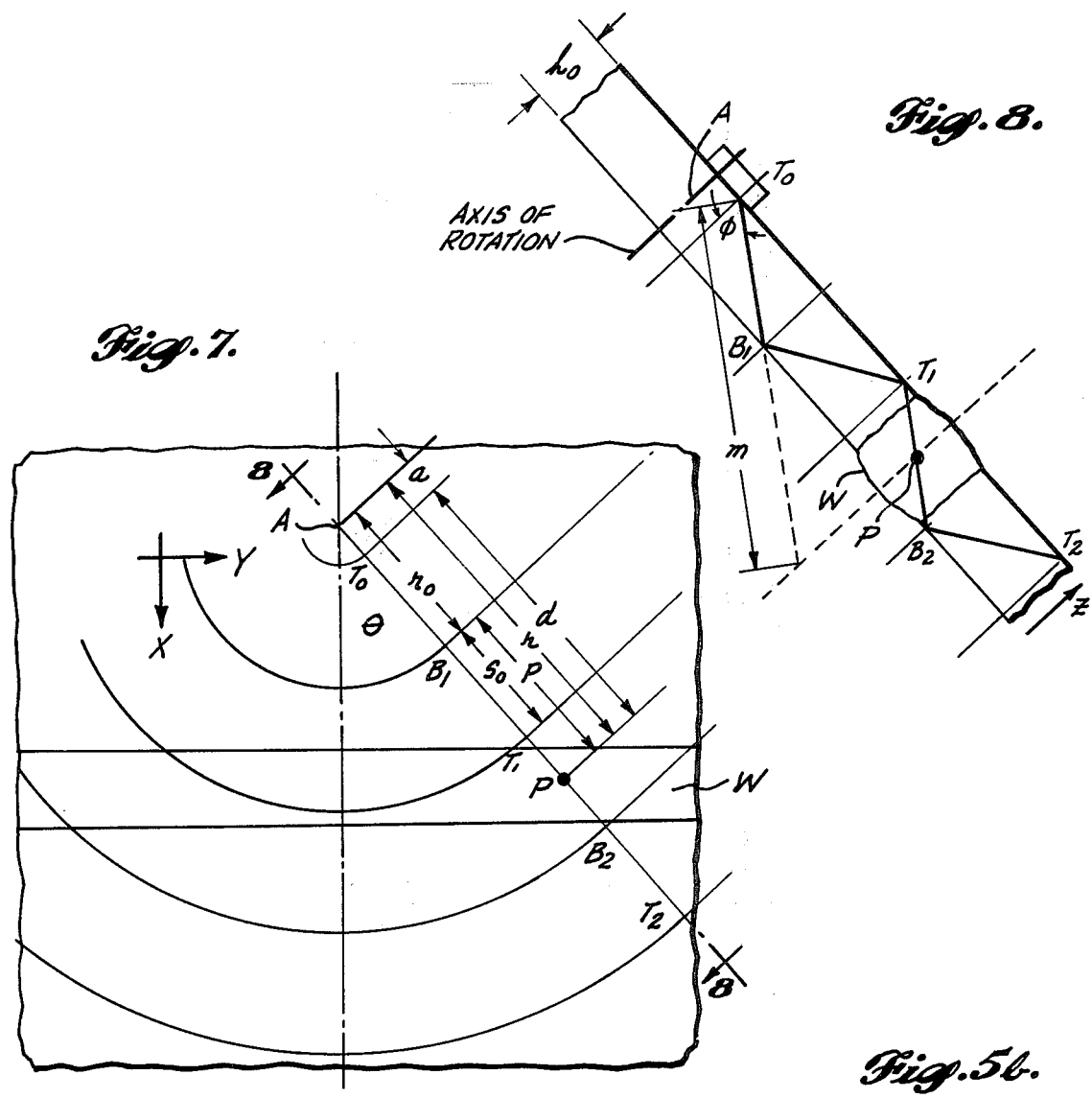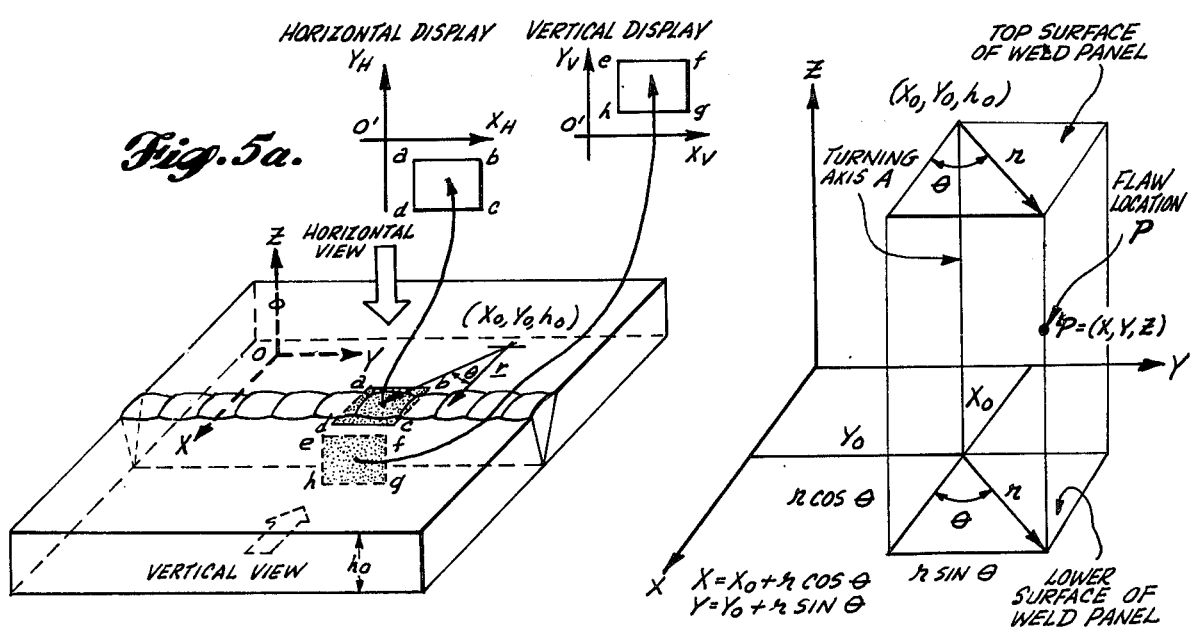

MECHANIZED SCANNING, DISPLAY AND RECORDING ULTRASONIC WELD INSPECTION SYSTEM

BACKGROUND OF THE INVENTION

This invention is directed to weld inspection and, more particularly, to ultrasonic weld inspection.

In certain environments, it is necessary that welds bonding two pieces of metal (e.g., panels) together be completely flawless so that no small discontinuities that will serve as "crack starters" exist. (Such discontinuities may grow into cracks under cyclic loading by "in service" forces, ultimately resulting in structural failure.) One technological area where welds having this degree of integrity are required is in ship building. In the past, such integrity has been required of ships' hulls. More recently, large hydrofoils developed for oceangoing hydrofoil ships require welds having a similar level of integrity. Obviously, the visual inspection of a weld cannot provide the assurance that the required weld integrity exists. That is, while visual inspection will detect large visable weld flaws, in general, minute weld flaws will not be detected. Further, visual inspection will miss even large flaws if they are totally located inside of the weld. For these reasons other techniques for inspecting welds to determine whether or not they possess an adequate level of integrity have been developed.

One such technique uses ultrasonic principles. In some ultrasonic systems an ultrasonic beam, produced by an ultrasonic transducer located on a surface of the welded part to be inspected, is directed toward the weld and specular beam reflections, caused by weld flaws, are detected. In the past, the ultrasonic transducers used in such systems have been manipulated by hand through a path of travel that is intended to ensure that the ultrasonic beam scans the entire weld volume to be inspected. The path is complex and may require moving the transducer both parallel to the weld at a relatively slow rate and transversely with respect to the center line of the weld. Simultaneously, the transducer is angularly oscillated back and forth. Usually, oil is spread on the surface of the welded part or panel to provide an ultrasonic beam coupling medium, and flaws are detected by watching for the appearances of peaks on a cathode ray tube (CRT) display, which denote the receipt of specular reflections created by the ultrasonic beam intersecting a weld flaw. Reflections having an amplitude exceeding a predetermined level are interpreted as rejectable flaw indications, unless they can be related to some known reflecting surface within the structure. If a rejectable flaw indication is found, the inspector manipulating the ultrasonic transducer attempts to identify the flaw, and usually marks its location directly on the weld.

While hand-scan methods have been successfully used to locate rejectable flaws in welds, this technique is unsatisfactory for a variety of reasons. For example, there is no way of assuring that freehand guidance of the transducer will result in 100% coverage of the weld volume. As noted above, the inspector is simultaneously required to: (1) manipulate the transducer in a complex scanning pattern; (2) ensure that sound is coupled uniformly into the test part; and (3) observe a complex oscilloscope trace to sort and analyze echo signals. Obviously, it is physically and mentally exhausting to perform these tasks over an extended period of time.

Further, it is impossible, using hand-scanning ultrasonic techniques, to obtain meaningful recordings of actual ultrasonic flaw indications (i.e., reflected signals) because it is impossible to sense the exact position of the hand and, thus, the exact position of the transducer, when a flaw echo signal is received. Obviously, recordings are helpful in identifying the kind of flaw that is producing a given signal and in separating marginal signals from background noise. Further, records free an inspector from having to continuously watch an oscilloscope trace, and ease the task of communicating the results of an inspection to other persons. Moreover, without recordings, it is difficult to prove that a given weld has actually been inspected. In addition, reproducibility is difficult to obtain using hand-scanning techniques. That is, it has been found that two different inspectors working on the same section of weld often obtain different results. Finally, freehand ultrasonic weld inspection is time-consuming, and therefore costly. In this regard, it has been found that an inspection rate of one-half hour per foot of weld is not uncommon.

In view of the foregoing difficulties, various proposals have been made to automate ultrasonic weld inspection. For a variety of reasons, the resultant systems have not been entirely satisfactory. In most instances, prior art mechanical ultrasonic weld inspection apparatus, capable of moving a transducer through a relatively complex path of travel, have not been portable. Other also relatively large and nonportable devices have used "immersion techniques", involving a large tank of water into which parts are immersed. Obviously, those devices have the disadvantage of requiring the time-consuming, and therefore costly, transportation of parts from an assembly area to an inspection area, and the subsequent return of the parts to the assembly area for removal of weld flaws or further assembly to other structures.

While some portable ultrasonic weld inspection devices have been proposed, these devices also have disadvantages. The primary disadvantage is their general inability to provide complex transducer motion. Specifically, such devices have generally provided orthogonal transducer motion, but not oscillatory transducer motion. Another disadvantage of many such devices is that, while portable, they are still large, heavy, and inflexible.

A further disadvantage of many types of prior art ultrasonic weld inspection systems, regardless of whether or not they are portable, is their inability to produce adequate displays and/or usable hard copy and video recordings.

Therefore, it is an object of this invention to provide a new and improved ultrasonic weld inspection apparatus.

It is a further object of this invention to provide a portable, mechanized scanning ultrasonic weld inspection system.

It is a another object of this invention to provide a portable mechanized scanning system suitable for moving a transducer through a complex path of travel.

It is a still further object of this invention to provide a new and improved display and/or recording subsystem for an ultrasonic weld inspection system.

It is yet another object of this invention to provide a mechanical scanning, display and recording ultrasonic weld inspection system.

SUMMARY OF THE INVENTION

In accordance with the present invention, a scanning mechanism for positioning an ultrasonic transducer on the surface of a part along orthogonal paths of travel, and oscillating the transducer over the surface, is disclosed. The orthogonal position of the transducer and the oscillatory pointing direction are continuously monitored, and the resultant position information is utilized to control the position of a related display beam or beams. More specifically, as the transducer is oscillated, it emits an ultrasonic beam at a predetermined angle into the part (e.g., panel) containing the weld being inspected. As the oscillating beam is reflected back and forth between parallel surfaces of the welded part through the weld, the entire weld volume is scanned. Flaws or faults in the weld create specular reflections that are returned to the transducer. These "flaw echoes" denote the presence of a flaw or flaws. The thusly produced position and presence information is used to control a visual display (and/or recorder, if desired).

In accordance with a preferred form of the present invention, the scanning mechanism includes an elongate track attachable to a welded part, so as to lie along a translation axis generally parallel to the longitudinal axis of the weld to be inspected. Mounted on the track for longitudinal movement is a translation carriage. Guide rods extending orthogonally outwardly from the translation carriage support an index carriage. The index carriage supports a sensor mechanism that includes an ultrasonic transducer adapted to ride on the surface of the part adjacent to, but spaced from, the weld to be inspected. Two electric motors, preferably stepping or DC motors, are mounted on the translation carriage. One motor moves the translation carriage longitudinally along the elongate track, and the other moves the index carriage orthogonally with respect to the elongate track, along the guide rods. The sensor mechanism includes a further stepping or DC motor mounted on the index carriage and connected to the transducer via an oscillatory coupling mechanism. The axis of oscillatory rotation may or may not coincide with the point where the ultrasonic beam enters the part.

In accordance with other aspects of a preferred embodiment of the invention, translation carriage and index carriage position information is provided by position sensors that continuously sense the movement, and thus the position, of these elements. Preferably, the position sensors are rotary potentiometers. Oscillatory information related to the oscillatory position of the transducer is continuously provided, either by a position sensor coupled to the shaft of the motor oscillating the transducer, or by a further motor driven in synchronism with the motor oscillating the transducer. In either case, the oscillating position information is converted into sine/cosine information prior to this portion of the position information being used to control the beam of the display.

In accordance with still further aspects of a preferred embodiment of the invention, the transducer is water-coupled to the surface of the body containing the weld to be inspected.

In accordance with yet other aspects of a preferred embodiment of the invention, the "flaw echo" display is displayed on a monitor subsystem. The monitor subsystem receives position information from the translation, index, and oscillatory position sensors, and flaw-presence information from the ultrasonic transducer. Preferably, the displayed flaw information is shaded in accordance with the magnitude of the received flaw echos. The monitor subsystem is adjusted such that the position information causes flaw presence information to be directly correlatable to the location of flaws in the weld. Preferably, two displays, either on separate display units or on a single, multiplexed display unit are provided. The two displays are orthogonal, with one being taken in the plane of the surface on which the transducer moves, and the other being orthogonal thereto and parallel to the weld. The display information can also be applied to a video recorder (or hard copy recorder), so that the display can be reproduced for later inspection, as desired. The displays are readily redeveloped during subsequent scans of the weld, since the motion or path of travel of the transducer, created by the mechanical scanning system, is readily reproducible. Thus the inaccuracies inherent in hand-transducer movement are eliminated. The path of travel can take on various forms, i.e., translation plus oscillation, index plus oscillation, etc., as desired.

In accordance with alternative aspects of this invention a pair of transducers, as opposed to a single transducer, are moved by the scanning mechanism. In this arrangement, rather than a single transducer transmitting an ultrasonic beam and receiving specular reflections, one of the pair of transducers transmits an ultrasonic beam and the other receives specular reflections created by weld flaws or faults, which do not return to the transmitting transducer. An adjustable mounting arrangement is provided so that the transducers can be positioned such that the receiving transducer is aligned with the weld region receiving the transmitted beam at all times. As with the single transducer arrangement, the scanning mechanism orthogonally positions, and oscillates, both transducers. In the dual transducer arrangement positioning (after alignment) and oscillating of the transducers occurs simultaneously.

It will be appreciated from the foregoing summary that the invention provides a new and improved ultrasonic weld inspection system. The scanning mechanism is portable and readily attachable to all planar, and many curved, panel surfaces containing a weld to be inspected. Preferably the elongate track is attached to the part by either magnets (on magnetic parts) or suction cups (on non-magnetic parts), even though other mechanisms may be utilized. The scanning mechanism is formed such that complex transducer motion, previously performed by hand, is performed by the scanning mechanism; and, the position of the transducer is known at all times. Since both position and flaw-presence information are provided, in the form of electronic signals, the information may be utilized to control a conventional beam display mechanism, such as a simple cathode ray tube display or a raster (TV monitor) display; or, recorded for future display. Further, the signals can be utilized to control permanent record (hard copy) recorders, such as ink jet, pen, etc., recorders. The invention provides displays in two orthogonal planes. One of the planes is the plane of transducer movement, and the other plane is through the part. Thus, one plane can be referred to as the horizontal plane (assuming the plane of transducer movement is generally horizontal), and the other as the vertical plane. The displays are image projections of the detected flaws in the display planes.

As will be readily appreciated by those skilled in the art and others from the foregoing discussion, the invention provides a system that overcomes the disadvantages of prior art systems. More specifically, because the scanning mechanism is portable, weld inspections can be performed at the part assembly location. Further, the part being inspected does not need to be immersed in water. Also, readily reproducible results are obtained using the invention. Finally, the various objections to movement of a transducer by hand are eliminated using the invention. Hence, the invention overcomes many of the disadvantages of prior art ultrasonic weld inspection systems discussed above.

BRIEF DESCRIPTION OF THE DRAWINGS

The foregoing objects and many of the attendant advantages of this invention will become more readily appreciated as the same becomes better understood by reference to the following detailed description when taken in conjunction with the accompanying drawings wherein:

FIG. 1 is a plan view generally illustrating the path of travel of a transducer moved by hand in accordance with prior art ultrasonic hand-scanning inspection procedures;

FIG. 2 is a schematic, cross-sectional view illustrating the idealized path of travel of an ultrasonic beam through a part and the weld to be inspected;

FIG. 3 is a perspective view of a scanning mechanism formed in accordance with the invention;

FIG. 4 is a schematic view of an apparatus for creating and maintaining an ultrasonic coupling water interface between an ultrasonic transducer and the surface over which it is moved;

FIGS. 5a and 5b are pictorial diagrams used to illustrate the orientation of the X,Y,Z planes used to describe the scanning/display interrelationship;

FIG. 6 is a pictorial diagram illustrating the display planes of an ultrasonic weld inspection display formed in accordance with the invention;

FIG. 7 is a plan view illustrating the scanning path of a transducer oscillating about an axis that is not coincident with the point of entry of the ultrasonic beam into the part containing the weld to be inspected;

FIG. 8 is a cross-sectional view along line 8—8 of FIG. 7;

DESCRIPTION OF THE PREFERRED EMBODIMENT

Figure 9:
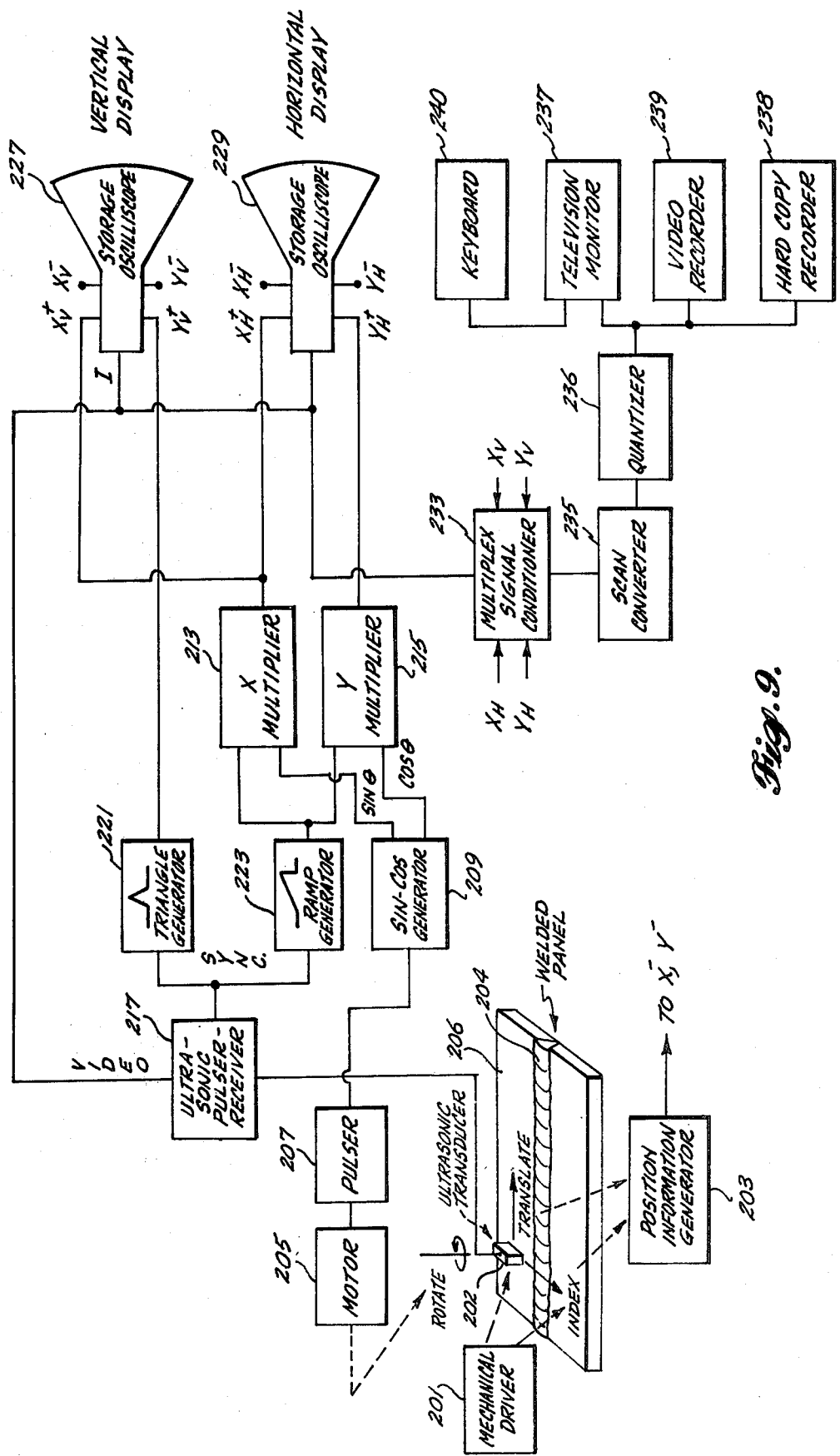
FIG. 9 is a partially block and partially schematic diagram of a mechanized scanning, display and recording ultrasonic weld inspection system formed in accordance with the invention.

As briefly discussed above, and as illustrated in FIG. 1, prior art manual ultrasonic weld inspection techniques generally require a weld inspector to move an ultrasonic transducer 21 over the surface of a panel 27, toward and away from a weld 29, and longitudinally parallel to the weld (generally along a zigzag path of travel 23), while simultaneously oscillating the transducer head (generally through an arc 25). As the transducer 21 is thusly moved, an ultrasonic beam 26 produced by the transducer scans the volume of the weld 29. The relatively complex scan path ensures that the entire volume of the weld 29 is scanned during the inspection sequence. As the ultrasonic beam 26 scans the weld 29, the beam is reflected by flaws or faults in the weld, resulting in the creation of flaw echoes. The flaw echoes return to the transducer generally along the same path of travel as the emitted beam. The transducer converts the flaw echoes to flaw signals that are displayed on an oscilloscope connected to the transducer, if they are above some predetermined minimum magnitude.

FIG. 2 illustrates the path of travel of the transducer beam through the panel 27 within which the weld 29 is located. The transducer 21 emits the ultrasonic beam 26 (which is actually a sequence of ultrasonic pulses) at a predetermined angle Q into the panel 27 at point $T_0$ located on one surface, illustrated as the upper surface. The beam 26 travels through the panel and impinges on the other (lower) surface of the panel at point $B_1$, where it is reflected back toward the upper surface where (at point $T_1$) it is reflected back toward the lower surface. This impingement/reflection sequence continues through the panel (i.e., from $T_1$ to $B_2$, from $B_2$ to $T_2$, etc.). Dotted line 26a and dash-dot line 26b illustrate paths of travel of the ultrasonic beam as the transducer is moved back and forth in a direction orthogonal to the longitudinal axis of the weld 29, denoted by the arrow 30. At some point in its path of travel, the beam 26 passes through the weld 29. Voids or faults along the beam path of travel create specular reflections, i.e., flaw echoes. The flaw echoes travel back to the ultrasonic transducer 21 and are utilized to control a display. By appropriate timing control (more fully described below with respect to FIGS. 7 and 8), only the flaw echoes created by weld faults or flaws are recognized and used to control the display. In the past, displays merely depicted a series of pulses, with the presence of a pulse being related to the presence of a flaw. The weld inspector, when a flaw echo pulse was displayed, determined the position of the flaw and identified the position on the panel to the best of his ability.

The present invention is directed to providing a mechanical scanner adapted to move a transducer along a path of travel that may be, but does not necessarily have to be, as complex as the transducer path of travel followed by weld inspectors manually moving a transducer. Even though not necessarily as complex, the path of travel may be as complex and, in any event, the available paths of travel are adequate to scan an entire weld volume. FIG. 3 illustrates a mechanical scanner formed in accordance with the invention.

The mechanical scanner illustrated in FIG. 3 generally comprises an elongate track 31, a translation carriage 33, and an index carriage 35. The elongate track 31 includes a hollow cylindrical shaft 37. Mounted atop the shaft 37 is an elongate rack support block 39. Mounted on the elongate rack support block 39 is a rack 41 having teeth, lying orthogonal to the axis of the shaft, formed in its upper surface. Affixed to the ends of the hollow shaft 37 are suction cup supports 43.

Each suction cup support 43 includes a mechanically actuated suction cup mechanism 45, i.e., a suction cup mechanism operated by a handle 47 such that when the handle is moved to a predetermined position, a flexible suction cup 49 is moved away from an adjacent surface enclosing the end of the cup, creating a suction force between the cup and the adjacent surface. Rotation of the handle 47 in the opposite direction releases the force. As will be readily appreciated from the following description, the suction cup supports form an attachment mechanism for attaching the mechanical scanner to a part. As such, the suction cup supports can be replaced by any other suitable mechanism, such as magnetic supports.

Each of the suction cup supports 43 includes an upwardly projecting bracket 51, through which the shaft of the related handle 47 passes. Mounted in the bracket 51, above the handle shaft 47 and orthogonal thereto, is a support shaft 53. Each support shaft 53 is rotatably mounted in its respective housing 51, and supports on one end a block 55. The ends of the hollow shaft 37 are rotatably mounted in the blocks 55.

Located on the sides of the blocks 55, remote from the sides receiving the hollow shaft 37, are U-shaped clamps 57. The U-shaped clamps 57 are affixed to the blocks 55. Mounted in a central aperture in the U-shaped clamps (aligned with the shaft 37) are knobs 59. Each knob is attached to the shaft 37 by a flat torsion spring 61. More specifically, one end of each flat torsion spring is affixed to an arm 63 projecting inwardly from its related knob 59. The torsion springs extend into the shaft from the knobs and are affixed to the interior of the shaft 37 at their other ends.

The flat torsion springs 61 are adapted to create an arcuate pressure tending to rotate the hollow shaft 37 in one direction. This pressure is counterbalanced by impingement of the hereinafter described transducer mounted on the index carriage 35 against the adjacent surface of the part containing the weld to be inspected. The pressure is created by rotating the knobs in the necessary direction, and thereafter tightening a locking bolt 64 passing through the open ends of the U-shaped clamps 57.

The translation carriage 33 includes a housing 65 in the general form of a right rectangular parallelepiped. The housing 65 includes a longitudinal aperture, having a cross-sectional shape similar to the cross-sectional shape of the hollow shaft 37, the rack support block 39 and the rack 41, through which these elements pass. Mounted on one side of the housing 65 (toward the rear as viewed in FIG. 3) is a first DC or stepping motor 67. The first motor 67 includes a shaft 69 that is rotatably supported by bearings 71 mounted in the translation carriage housing 65. The first motor is positioned such that the longitudinal axis of the shaft 69 lies orthogonal to, and above, the rack 41. Mounted on the shaft 69 of the first motor 67, inside of the housing and thus not viewable, is a gear coupled to the rack 41. The coupling is such that when the first motor 67 is energized, the rotation of the shaft via the interaction between the gear and the rack 41 causes the housing 65 to move longitudinally along the hollow shaft 37 in one direction or the other, depending on the direction of rotation of the motor shaft. This type of longitudinal motion is herein referred to as translation movement.

Projecting upwardly from the housing 65, generally coplanar with the side on which the first motor 67 is mounted, is a bracket 73. Mounted on the bracket 73 is a first rotary potentiometer 75. The first rotary potentiometer 75 projects outwardly (rearwardly) from the housing 65, and includes a shaft 77 rotatably mounted in the arm 73. The axis of the shaft 77 lies orthogonal to, and above, the longitudinal axis of the hollow shaft 37.

The outer end of the shaft is rotatably mounted in a second bracket 74 mounted atop the housing 65. Mounted on the potentiometer shaft 73, above the rack 41, is a first gear 79. The first gear is coupled via a pair of idler gears 81 and 83, rotatably mounted in the housing and appropriately aligned, to the rack 41. Thus, as the first motor 67 moves the translation carriage housing 65 longitudinally along the hollow shaft 37 in the manner previously described, the shaft 77 of the first rotary potentiometer 75 is rotated. Rotation of the shaft 77 causes the potentiometer 75 to control a position-related signal in a conventional manner. Thus, information related to the position of the housing 65 along the longitudinal (translation) axis defined by the hollow shaft 37 is provided.

Projecting orthogonally outwardly from the side of the translation carriage housing 65, remote from the side on which the first stepper motor 67 is mounted and above the hollow shaft 37, are a pair of parallel guide rails 85. Mounted on the parallel guide rails 85 is the index carriage 35. More specifically, the index carriage 35 includes a generally flat bracket 87 through which the guide rods 85 pass.

Mounted on the same side of the translation carriage housing 65 as the first motor 67 is a second DC or stepping motor 69. Preferably the first motor is mounted near one end of the housing 65 and the second motor is mounted near the other end. The second motor includes a shaft that also lies orthogonal to, and above, the longitudinal axis of the hollow shaft 37.

Affixed to and extending axially outwardly from (or forming a unitary part of) the shaft of the second motor is a lead screw 89. Thus, the lead screw 89 lies parallel to, and preferably between, the guide rails 85. The lead screw is rotatably mounted in bearings 93 suitably positioned in the translation carriage housing 65, and extends to and is rotatably threaded into a nut 91 fixedly mounted in a suitable position in the bracket 87 of the index carriage 35. In operation, when the second motor 69 is energized so that its shaft rotates, the lead screw 89 also rotates. Since the lead screw 89 is threaded into a nut 91 affixed in the bracket 87 of the index carriage 35, rotation of the lead screw moves the index carriage 35 longitudinally back and forth along the guide rails 85. This direction of movement is herein referred to as index or indexing movement. Since the axes of the guide rails lie orthogonal to the longitudinal axis of the hollow shaft 37, it will be appreciated that the mechanism thus far described produces X-Y or orthogonal longitudinal motion.

One end of an index rack 95 is affixed to the upper surface of the translation carriage housing 65 by an L-shaped bracket 97. The index rack 95 is positioned such that it extends orthogonally outwardly from the housing 65 in a direction parallel to, and above, the guide rails 85 and the lead screw 89. The rack 95 includes teeth that lie in a generally vertical plane.

Extending upwardly from atop the generally flat bracket 87 of the scanning mechanism 35, parallel to the edge nearest the translation carriage housing 65, is a support block 99. An arm 101 is affixed to the upper end of the support block 99 and projects outwardly from a corner of the support block 99 toward the translation carriage housing so that its outer end lies above the rack 95. Mounted atop the outer end of the arm 101 is a second rotary potentiometer 103. The second rotary potentiometer 103 includes a shaft 105 that projects vertically downwardly through the arm 101, toward the rack 95. A gear 107 affixed to the lower end of the shaft 105 is positioned so as to mesh with the teeth of the rack 95. Thus, as the index carriage 35 is moved back and forth as the second motor 69 is energized, the second rotary potentiometer 103 controls an electrical signal, such that the signal has a voltage or current value related to the position of the index carriage 35.

It will be appreciated from the description thus far that a mechanism for moving the generally flat bracket 87 orthogonally in two directions has been described. The following description describes an ultrasonic transducer mechanism supported by the index carriage. The ultrasonic transducer mechanism is adapted to support and move an ultrasonic transducer 111 in an oscillatory manner over the surface of the part to which the suction cups 45 are attached.

Affixed to, and projecting from, the support block 99 of the index carriage 35 is an upper arm 113. The upper arm extends outwardly from the side of the support block 99 remote from the side facing the translation carriage housing 65, near the top of the support block. Thus, the upper arm 113 overlies the top of the generally flat bracket 87 and is spaced therefrom. Mounted in the generally flat bracket 87, and extending between that bracket and the upper arm, is a speed reducer gear box 115. The axis of rotation of the speed reducer is vertically oriented, and its lower shaft is connected to a third DC or stepping motor mounted beneath the generally flat bracket 87. The third motor per se cannot be seen in FIG. 3, since it is mounted inside of a finned heat sink 117. Affixed to the upper end of the upper shaft 121 of the speed reducer 115, so as to lie above the upper surface of the upper arm 113, is a crank collar. Attached to the crank collar 119, a predetermined radial distance from the center of the upper shaft 121 of the speed reducer 115, is one end of a connecting link 123.

A lower arm 125 projects outwardly and downwardly from the flat housing 87 in a stepped manner and terminates in a flange 127 that lies beneath the outer end of the upper arm 113. Rotatably mounted in bearings, between the flange 127 and the outer end of the upper arm 113, is a nodder shaft 129. Thus, the nodder shaft is rotatable about a generally vertical axis. A second crank collar 131 is attached to the upper end of the nodder shaft 129, above the upper surface of the upper arm 113. The other end of the link 123 is connected to the second crank collar 131, a predetermined radial distance from the axis of rotation of the nodder shaft 129. The radial distance between the rotational axis of the nodder shaft 129 and the point of attachment of the associated end of the link 123 to the second crank collar 131 is substantially greater than the radial distance between the rotational axis of the upper shaft 121 of the speed reducer 115 and the point of attachment of the related end of the link 123 to the first crank collar 119. Because of this radial difference, each time upper shaft 121 rotates through a complete revolution, the nodder shaft 129 oscillates or nods back and forth over a predetermined arcuate distance (e.g., 45 degrees). The exact arcuate distance is determined by the difference in radial distances.

The ultrasonic transducer 111 is connected to the lower end of the nodder shaft 129 via a universal joint mechanism 133. The universal joint mechanism includes a rectangular parallelepiped block 135 affixed to the lower end of the nodder shaft 129 beneath the flange 127 of the lower arm 125. A rectangular frame 137, lying in a generally horizontal plane, surrounds the block 135. A pair of pins, lying along a common axis and located on opposite sides of the rectangular frame 137, rotatably affix the frame 137 to the block 135. Projecting downwardly from the sides of the frame, opposed to the sides pinned to the block 135, are vertical arms 141. The lower ends of the vertical arms 141 are connected by a pair of coaxial pins 143 to a transducer frame 145. The transducer frame 145 surrounds the transducer 111. The specific manner of mounting the transducer 111 in the transducer frame is best illustrated in FIG. 4 and more fully hereinafter described.

It will be appreciated from the foregoing description of the universal joint mechanism 133 that one set of pins allows the transducer 111 to move in one plane and the other allows it to move in an orthogonal plane. The rotatable mounting of the hollow shaft 37 in the blocks 55 and the spring pressure (created by the flat springs 61) allows some vertical freedom of movement. Thus, as the transducer is moved over a surface, it is free to follow changes in surface curvature without the transducer 111 losing contact with the surface.

Mounted atop the upper arm 113, adjacent to the first crank collar 119, is a linear potentiometer 147. The linear potentiometer 147 is coupled to the upper shaft 121 of the speed reducer 119 via any suitable means, such as gears, chain belt, etc., (not shown), and driven thereby. Thus, as the crank collar 119 rotates and causes the transducer 111 to oscillate, the linear potentiometer 147 controls a linearly related position signal. The position signal is utilized to provide suitable sinusoidal information via, for example, an analog-to-digital converter connected to a programmable read-only memory (PROM) programmed to produce sine and cosine information in accordance with a related digital input. An alternative technique for providing sine and cosine information is to drive an auxiliary DC or stepping motor synchronously with the motor driving the speed reducer and connect the shaft of the auxiliary motor to a sine-cosine resolver adapted to produce sine and cosine output signals in accordance with the position of the shaft. Regardless of how produced, the sine and cosine signals define the position of the transducer 111 as it is being oscillated.

In order to prevent runaway translation movement of the translation carriage 33 one or two stop clamps 151, attachable to the hollow shaft, at either or both ends thereof are provided. The stop clamps activate microswitches (not shown) that turn off the first (translation) motor 67. Further, in order to terminate inward (i.e., toward the translation carriage) movement of the index carriage 35, a microswitch 153, series-connected to the second stepping motor, is mounted atop the translation carriage housing 65 in a position such that the activating arm 155 of the microswitch is activated by the rear surface of the block 99 mounted atop and near the rear of the generally flat bracket 87. Activation of this switch turns off the second (index) motor 69.

It will be appreciated from the foregoing description that the mechanical scanner illustrated in FIG. 3 is adapted to move or position the transducer 111 along orthogonal, longitudinal axes of travel and oscillate the transducer on the surface of a part having a weld to be inspected whereby the scanning path illustrated in FIG. 1 can be followed, if desired. The complex FIG. 1 path is followed if the three motors are all operated at suitable times. As an alternative, the motor 67 moving the translation carriage housing 65 may be indexed, and both the motor 69 moving the index carriage 35 and the motor moving the nodding shaft 129 operated continuously. Still further, the second motor 69 may be entirely deactivated and only the first and third motors activated, whereby only translation and oscillation motions occur. Such a path could be followed until a fault is located. Thereafter, an index path could be followed (along with transducer oscillation) to better define the fault. Thus, various paths of travel can be followed, as desired.

Although not fully illustrated in FIG. 3 for reasons of clarity, the ultrasonic transducer 111 is water-coupled to the surface of the welded panel over which it is to be moved. FIG. 4 illustrates in pictorial form an apparatus for liquid-coupling the transducer 111 to the panel. In addition to including the transducer 111 and its supporting frame 145, FIG. 4 also includes a container 157 housing a suitable source of liquid, such as water. A suitable airhole 158 is located in the top of the container so that a siphon 159 can be used to withdraw the liquid. A tube 160 extends from the container siphon 159 to a tubular connector 161 extending through the frame 145 to the interior thereof. More specifically, preferably the frame 145 is formed of a suitable low friction material such as nylon. The upper region of the frame 145 tightly surrounds the ultrasonic transducer 111, which may be a right rectangular parallelepiped in form.

The lower region of the frame includes an enlarged aperture having interior vertical walls 163 spaced from the external vertical walls of the transducer 111. The tubular connector 161 communicates with the enlarged aperture, whereby fluid lies between the transducer 111 and the walls 163 of the aperture. In addition, the plane of the lower surface of the frame 145 is located beneath the lower surface of the transducer 111 by a distance "a", whereby a film of water lies beneath the transducer. This film provides a fluid coupling that couples the ultrasonic beam to the panel on which the transducer is located. The transducer 111 is held in place by bolts or pins 165 extending through the walls of the frame in the region where the frame tightly surrounds the transducer 111.

As will be appreciated by those skilled in the art and others, the frame, if it is formed of nylon or some other similar material, will wear away as it is moved over the surface of a part. Thus, after a period of time the space "a" between the lower surface of the transducer 111 and the lower surface of the frame 145 will decrease. The invention provides a means for compensating for such wear. Specifically, the bolts 165 are first loosened. Then a shim of thickness "a" is placed beneath the transducer 111, and the entire assembly is placed on a planar surface. Thereafter, the transducer 111 is moved vertically until the shim just fills the space between the transducer and the planar surface. Then, the bolts 165 are tightened. In this manner, initial adjustment, and adjustment for transducer frame wear, is accomplished.

In accordance with the invention, the information derived from the mechanical scanner (i.e., position and presence of flaw information) is utilized to control either a display or a recording system, or both. The displays may be in the form of storage oscilloscope displays or television monitor displays, and the recording system may comprise a video recorder or a hard-copy recorder. FIG. 9 is a partially block and partially pictorial diagram, illustrating an electronic system formed in accordance with the invention, for controlling such displays and recorders.

Prior to describing the system illustrated in FIG. 9 in detail, a geometric description of how a cathode ray tube beam display in controllable to provide two orthogonal displays (horizontal and vertical) depicting the presence and location of flaws or faults in a weld is provided. In this regard, attention is directed to FIGS. 5-8. FIG. 5a and 5b illustrate a three-dimensional Cartesian coordinate (X,Y,Z) orientation system. In this system, the X-Y display plane is the plane of the part or panel containing the weld and is referred to herein as the horizontal display or view plane. The Y-Z display plane is a plane orthogonal to the X-Y display plane and parallel to the weld, and is herein referred to as the vertical display or view plane.

As illustrated in FIG. 6, the horizontal and vertical display or view planes display fault projections. More specifically, FIG. 6 illustrates two weld faults or flaws—F1 and F2. When suitably projected, these faults or flaws create horizontal projections HF1 and HF2, respectively, in the X-Y display plane; and vertical projections VF1 and VF2, respectively, in the Y-Z display plane. These are the types of displays created on a cathode ray tube display surface (or a hard-copy record medium) by the invention.

FIG. 7 is a plan (hoizontal view) of an ultrasonic beam at a point in an oscillating scan where a fault or flaw P is present in a weld W. FIG. 8 is a cross-sectional view through the weld and lying along the beam path, i.e., FIG. 8 is a cross-sectional view encompassing the axis of rotation A of the transducer and the flaw point P. FIG. 8 illustrates an embodiment of the invention wherein the point at which the beam enters the panel, $T_O$, lies between the rotation axis and the weld W. The following mathematical analysis is applicable not only to this embodiment, but also to coincident embodiments and embodiments where the axis of rotation lies between the beam entry point, $T_O$, and the weld W.

Prior to describing the geometrical relationship between the ultrasonic beam and a CRT beam, it must be understood that a relationship between ultrasonic travel time and distance exists in both display planes. In this regard, flaw signal arrival time is equal to the time (t) it takes for sound to travel from $T_O$ to P and back again, plus the total travel time between the transducer and the surface of the panel, i.e., the time of travel through a lucite block that forms a part of the transducer, plus the time of travel through the coupling medium, the latter time being substantially negligable. The transducer/surface travel time is a constant and may be referred to as K. Thus if a transmission pulse occurs at time equal zero (0):

$$t = \frac{2m}{v} + K \tag{1}$$

where:

M = distance covered by beam from $T_O$ to P and back to $T_O$

V = velocity of sound in the panel

In FIGS. 7 and 8, m is geometrically shown to be equal to a straight line (since angles of sound incidence and reflection off of the top and bottom surfaces of the panel are the same) equal to $d/\sin \phi$, where $\phi$ equals the complement of the angle of entry, i.e., $\phi$ equals the angle the beam path makes with a line normal to the face of the transducer; and, d equals the distance between $T_O$ and P in the horizontal plane. Combining this relationship with Equation (1) results in the following equation:

$$t = \frac{2d}{v\sin\phi} + K \quad (2)$$

As shown in FIG. 7: $d=r-a$; where: $r=$ distance between the axis rotation of the transducer and P in the horizontal plane; and, $a=$ distance between the axis or rotation of the transducer and $T_O$ in the horizontal plane. Thus Equation (2) can be restated as:

$$t = \frac{2(r-a)}{v\sin\phi} + K \quad (3)$$

since $2a/v \sin\phi$ equals a constant, $K_1$, Equation (3) can be restated as:

$$t = \frac{2}{v\sin\phi}r + K_2 \quad (4)$$

where $K_2 = K - K_1$ or, since $2/v \sin\phi$ equals a constant, $K_3$, Equation (4) can be restated as:

$$t = K_3 r + K_2 \quad (5)$$

Thus, it has been shown that except for constant $K_2$, the time between the transmission of a pulse and the receipt of a flaw echo, and the distance from the turning center A to the projection of P in the horizontal plane, are directly related by $K_3$.

Turning now to a discussion of the geometrical relationship between the ultrasonic beam direction and the direction of a CRT beam; as discussed above, P is the location of a flaw or fault (beam scattering center); and t is the time between transmission of an ultrasonic pulse and the receipt of an echo. It will be appreciated that the position of the transducer at the time a fault or flaw produces an echo point can be defined as $X_o$, $Y_o$, and the rotation angle (i.e., the angle between a line orthogonal to the weld passing through the transducer axis of rotation and the direction of the beam, in the horizontal plane—(see FIG. 7) can be defined as $\theta$. When the transducer position and the beam "angle" are so defined, the X,Y,Z position of P can be defined by the following equations:

$$X = X_o + r\cos\theta \quad (6)$$

$$Y = Y_o + r\sin\theta \quad (7)$$

$$Z = \begin{cases} h_o\left[\dfrac{r-r_o}{s_o}\right] & \text{when } P \text{ is between } B_1 \text{ and } T_1 \\ h_o\left[2 - \dfrac{r-r_o}{s_o}\right] & \text{when } P \text{ is between } T_1 \text{ and } B_2 \end{cases} \quad (8)$$

where:
$h_o=$ thickness of the panel, i.e., the vertical distance between the beam-flecting surfaces
$r_o=$ distance between A and $B_1$ in the horizontal plane coincident with the upper surface of the part
$s_o=$ distance between $B_1$ and $T_1$ (or $T_1$ and $B_2$, etc.) in the horizontal plane and,
r is as defined above.

Since X,Y define the position of the fault in the horizontal plane, $P_H=(X,Y,O)$; and, since Y,Z define the position of the fault in the vertical plane $P_V=(O,Y,Z)$, the foregoing formulas hold true regardless of whether $T_O$ is between A and W, coincident with A, or A is located between $T_O$ and W. In the latter case, the turning axis could, for example, pass through $T_1$ if desired. As will be understood by those skilled in the art, such an arrangement may, in many situations, be more desirable than the illustrative arrangement shown in FIGS. 7 and 8.

As will be readily understood by those in the CRT display art, the desired horizontal and vertical displays could be presented on separate display devices, or they could be multiplexed and displayed on a single display device. Either display type can use storage CRT's, if desired, or either display could take the form of a television monitor (which has a raster) if the information is scan-converted prior to application to the monitor. Since a single display device is somewhat more economical and useful, the following discussion is directed to such a device. However, it should be recognized that the discussion is equally applicable to a dual-display device arrangement.

During the "horizontal view" phase of a multiplexed display, signals denoted $H_x$ and $H_y$ are applied to the X and Y deflection amplifiers, respectively, and during the "vertical view" phase signals denoted $V_x$ and $V_y$ are so applied, respectively. During either phase, a pulse I is applied to the intensity modulation amplifier when a pulse echo is received, i.e., at time t after the pulse is transmitted. The intensity of I is related to the intensity of the received echo. If the display tube is a storage tube, a quantity of charge, proportional to the echo amplitude, will be stored at locations:

$$(X_H, Y_H) = K[H_x(t), H_y(t)] \quad (9)$$

$$(X_V, Y_V) = k[V_x(t), V_y(t)] \quad (10)$$

on the face of the storage tube, where k is a constant determined by the gain of the related amplifiers, and, $I_H$ and $I_V$ are the horizontal and vertical intensities, respectively. (If the tube is a non-storage tube, the displays will occur; however, they will not be "stored," unless refreshed by a fast rescan containing the same display information.) The foregoing holds true as long as the multiplex period is much shorter than the mechanical oscillation period. In this manner, each fault produces two displays—a horizontal display at $(X_H, Y_H)$, and a vertical display at $(X_V, Y_V)$.

Next, $H_x(t)$, $H_y(t)$, $V_x(t)$, and $V_y(t)$ are defined such that they will vary in accordance with the following electronically realizable equations:

$$H_y(t) = -H_oX_o - (t-\tau)\alpha\cos\theta\tau \leq t \leq t_3 \text{ zero otherwise} \quad (11)$$

$$H_x(t) = H_oY_o + (t-\tau)\alpha\sin\theta\tau \leq t \leq t_3 \text{ zero otherwise} \quad (12)$$

$$V_x(t) = H_oY_o + (t-\tau)\alpha\sin\theta\tau \leq t \leq t_3 \text{ zero otherwise} \quad (13)$$

$$V_y(t) = \begin{cases} (t-t_1)\beta & \text{for } t_1 \leq t \leq t_2 \\ (t_3-t)\beta & \text{for } t_2 \leq t \leq t_3 \end{cases} \text{; zero otherwise} \quad (14)$$

where:

$t_1$ = time of arrival of a pulse returned by a flaw located at $B_1$ $t_2$ = time of arrival of a pulse returned by a flaw located at $T_1$ $t_3$ = the time of arrival of a pulse returned by a flaw located at $B_2$ $(t-\tau)\alpha$ is a ramp of slope $\alpha$ and delay $\tau$ the $V_y(t)$ equations define a triangular wave of slope $\beta$ running from $t_1$ to $t_3$ with a vertex at $t_2$ all other signals are DC voltages proportional to $X_o$, $Y_o$, $\cos\theta$, and $\sin\theta$ as these terms are defined above.

Combining Equations (9)–(10) with (11)–(14) results in the following equation being produced:

$$Y_H = -kH_oX_o - k(t-\tau)\alpha \cos\theta \qquad (15)$$

$$X_V = X_H = kH_oY_o + k(t-\tau)\alpha \sin\theta \qquad (16)$$

$$Y_V = \begin{cases} k(t-t_1)\beta & \text{for } t_1 \leq t \leq t_2 \\ k(t_3-t)\beta & \text{for } t_2 \leq t \leq t_3 \end{cases} \qquad (17)$$

Substituting the definition of t from Equation (5) into Equations (15)–(17) results in the following equations:

$$Y_H = -kH_oX_o - k\alpha(K_3r + K_2 - \tau)\cos\theta \qquad (18)$$

$$X_V = X_H = kH_oY_o + k\alpha(K_3r + K_2 - \tau)\sin\theta \qquad (19)$$

$$Y_V = \begin{cases} k\beta(K_3r + K_2 - t_1) & \text{for } t_1 \leq t \leq t_2 \\ k\beta(t_3 - K_3r - K_2) & \text{for } t_2 \leq t \leq t_3 \end{cases} \qquad (20)$$

As will be readily appreciated, since $H_o$, $\alpha$, $\beta$, $\tau$, $t_1$ and $t_3$, are adjustable DC voltages, they are parameters that are available for adjustment. Thus, they can be selected in terms of constants, to be as follows:

$$H_o = 1/k \qquad (21)$$

$$\alpha = 1/kK_3 \qquad (22)$$

$$\beta = h_o/kK_3s_o \qquad (23)$$

$$\tau = K_2 \qquad (24)$$

$$t_1 = K_3r_o + K_2 \qquad (25)$$

$$t_3 = K_3(r_o + 2s_o) + K_2 \qquad (26)$$

As a result, equations (18)–(20) can be rewritten as:

$$Y_H = -k\left[\frac{1}{k}\right]X_o - k\left[\frac{1}{kK_3}\right][K_3r + K_2 - K_2]\cos\theta \qquad (27)$$

$$X_v = X_H = k\left[\frac{1}{k}\right]Y_o + k\left[\frac{1}{kK_3}\right][K_3r + K_2 - K_2]\sin\theta \qquad (28)$$

$$Y_V = \begin{cases} k\left[\dfrac{h_o}{kK_3s_o}\right][K_3r + K_2 - K_3r_o - K_2] \\ k\left[\dfrac{h_o}{kK_3s_o}\right][K_3(r_o + 2s_o) + K_2 - K_3r - K_2] \end{cases} \qquad (29)$$

which simplify to:

$$Y_H = -X_o - r\cos\theta \qquad (30)$$

$$X_H = X_V = Y_o + r\sin\theta \qquad (31)$$

$$Y_V = \begin{cases} h_o\left[\dfrac{r - r_o}{s_o}\right] & \text{for } t \text{ between } t_1 \text{ and } t_2 \\ h_o\left[2 - \dfrac{r - r_o}{s_o}\right] & \text{for } t \text{ between } t_2 \text{ and } t_3 \end{cases} \qquad (32)$$

Therefore:

$$\begin{aligned} X_H &= Y \\ Y_H &= -X \end{aligned} \qquad (33)$$

$$\begin{aligned} X_V &= Y \\ Y_V &= Z \end{aligned} \qquad (34)$$

A geometric representation of the foregoing transformations is illustrated in FIGS. 5a and 5b. In accordance with the foregoing analysis flaw indications ($I_H$) coincide with a flaw projections ($P_H$), i.e., $P_H \rightarrow I_H$ where $P_H(X,Y,0)$ is the site of a flaw projection and $I_H$ is the site of a flaw indication. In this regard, it will be observed that if a horizontal display is superimposed over the projection illustrated in FIG. 5b along the space axes 0' over 0, $Y_H$ along $-X$ and $X_H$ along Y, the resultant flaw indication will coincide with the illustrated flaw projection. Since a pattern of flaw projections is a collection of individual flaw points, this pattern will coincide with a pattern of flaw indications. The two patterns are therefore, the same. Obviously, the same discussion applies to the vertical display if 0' is placed over 0, $Y_V$ along Z and $X_V$ along Y. Stated in words, the image location on the display tube for the horizontal display can be made identical to the location of a fault projected into a horizontal plane; and, the image location on the display tube for the vertical display can be made identical to the location of a fault projected into a vertical plane. All that needs to be done to provide this relationship is to provide a system that functions in accordance with Equations (15)–(17); and, make the appropriate adjustments described above. A suitable system is illustrated in FIG. 9 and hereinafter described.

FIG. 9 illustrates, in functional block form, a mechanical driver 201 adapted to translate an ultrasonic transducer 202 parallel to a weld 204 formed in a panel 206, and also index the transducer orthogonal to the weld. In addition, a position information generator 203, also illustrated in functional block form, is coupled to the transducer to produce information regarding the position thereof along the translation and index axes. Further, a motor 205 is illustrated as coupled to the transducer 202 to oscillate the transducer over the upper surface of the panel 206. It will be appreciated that the scanning mechanism illustrated in FIG. 3 is an apparatus that performs the functions of the mechanical driver 201, the position information generator 203, and the motor 205.

Also illustrated in FIG. 9 is a pulser 207 connected to the motor 205 and to a sine-cosine generator 209. Both the motor and the sine-cosine generator simultaneously receive pulses produced by the pulser 207. Assuming the motor is a stepping motor, it "steps" upon receipt of a pulse; and the sine-cosine generator, upon receipt of a pulse, produces related sine and cosine output signals. The sine signal is applied to the input of a X (horizontal) multiplier 213, and a cosine signal is applied to the input of a Y (vertical) multiplier 215.

The ultrasonic transducer 202 is connected to an ultrasonic pulser-receiver 217. The ultrasonic pulser-receiver both produces pulse signals and receives echo signals. The electrical pulse signals produced by the pulser-receiver are converted by the ultrasonic transducer into ultrasonic pulses and applied to the panel 206 in the manner previously described. Echoes received by the ultrasonic transducer are converted into electrical echo signals by the ultrasonic transducer and applied to the ultrasonic pulser-receiver.

The ultrasonic pulser-receiver transmits a sync pulse to a triangle generator 221 and a ramp generator 223 each time an ultrasonic pulse signal is produced. The echo signals received by the ultrasonic pulser-receiver are converted into video signals and applied to the intensity inputs (I) of a vertical display storage oscilloscope 227 and a horizontal display storage oscilloscope 229. The intensity inputs, of course, control the intensity of the display and are normally referred to as the Z-axis inputs of a CRT.

The output of the triangle generator 221 is connected to the positive Y input of the vertical display storage oscilloscope 227 (i.e., the $Y_V^+$ input). The output of the ramp generator 223 is connected to the second inputs of the X and Y multipliers 213 and 215. The output of the X multiplier 213 is connected to the positive X inputs of the vertical and horizontal display storage oscilloscopes (i.e., the $X_V^+$ and $X_H^+$, inputs respectively). The output of the Y multiplier 215 is connected to the positive Y input of the horizontal display storage oscilloscope (i.e., the $Y_H^+$ input). The position information circuit 203, as noted above, produces transducer translation and index axis position signals. These signals are applied to the appropriate negative X and Y inputs of the vertical and horizontal display storage oscilloscopes 227 and 229 (i.e., the $X_V^-$, $Y_V^-$, $X_H^-$, and $Y_H^-$ inputs).

It will be appreciated from viewing FIG. 9 and the foregoing description that the signals applied to the negative X and Y inputs of the storage oscilloscopes control the respective beam positions with respect to the translation and index positions of the transducer. Thus they contain $kH_oX_o$ and $kH_oY_o$ [Equations (15) and (16)] information. The signals applied to the positive X and Y inputs control the respective beam positions with respect to the oscillation position of the transducer. Thus these inputs contain the $k(t-\tau)\alpha \cos\theta$, $k(t-\tau)\alpha \sin\theta$ and $k(t-T_1)\beta$ or $k(t_3-t)\beta$ [Equations (15), (16), and (17)] information.

While FIG. 9 illustrates separate horizontal and vertical storage oscilloscopes, it will be readily appreciated that a single storage oscilloscope can be utilized. Either a "dual beam" scope or a single-beam scope can be used. In the latter case, obviously, the position ($X_V$, $X_H$, $Y_V$, $Y_H$) and presence (I) information must be suitably multiplexed prior to application to the scope.

In addition to providing horizontal and vertical storage oscilloscope displays, the invention also can provide alternative (or additional) television monitor displays or form video or hard-copy records. In this regard, as illustrated in FIG. 9, the output of the ultrasonic pulser receiver 217, which contains flaw presence information, is connected to the input of a multiplex signal conditioner. The multiplex signal conditioner also receives the various $X_H$, $Y_H$, $X_V$ and $Y_V$ (both positive and negative) signals, which contain transducer position information. The multiplex signal conditioner multiplexes and conditions the signals it receives and applies them to a scan converter 235. The scan converter converts the signals into a form suitable for controlling the "picture" on a TV monitor. The TV monitor may, for example, have a conventional 525 line interlaced raster. A suitable scan converter is the Model 639 Scan Converter produced by Hughes Aircraft Company, Industrial Products Divison, Oceanside, Calif.

Figure 10:
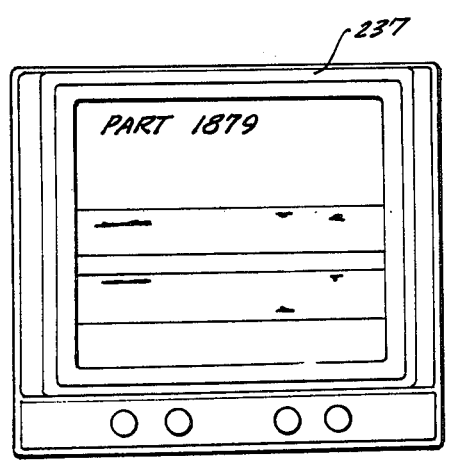
FIG. 10 is a pictorial view of the face of a TV monitor displaying the position and presence information derived by the mechanized scanning, display, and recording ultrasonic weld inspection system illustrated in FIG. 9; and, FIG. 11 is a pictorial diagram of a dual transducer embodiment of a sensor mechanism formed in accordance with the invention.

The output of the scan converter is connected to a television monitor 237 and to a video recorder 239 via a quantizer 236. If desired, the output of the scan converter can also be applied to a hard-copy recorder 238 as a further alternative (or addition). Also illustrated in FIG. 9 is a keyboard 240 connected to the television monitor 237. The keyboard allows certain information, such as a part identification number, to be displayed simultaneously with the weld fault or flaw display (see FIG. 10). If desired, the keyboard can also be connected to the video recorder 239 and to the hard-copy recorder 238 to create similar information on the records produced by these items.

As will be readily appreciated from the foregoing description and FIGS. 1-9 the invention provides a mechanized scanning, display and recording ultrasonic weld inspection system that includes a scanning mechanism subsystem and an electronic monitoring subsystem. The monitoring subsystem is adapted to display weld flaws or faults projected onto horizontal and vertical display planes. The scanning mechanism is adapted to selectively move an ultrasonic transducer along a predetermined path of travel. The path of travel includes selected movement along a translation axis, selected movement along an index axis and oscillatory movement of the transducer. The transducer emits ultrasonic pulses that penetrate the panel within which the flaw is located. The penetrating ultrasonic pulses form an ultrasonic beam that scans the weld. Subsequent to the emission of an ultrasonic pulse, the transducer is adapted to look for the specular reflections caused by faults or flaws in the weld. These specular reflections or echos are used to control the intensity of an electron beam of a cathode ray tube display system, which may be a storage oscilloscope or a TV monitor. Alternatively, or in addition, this "flaw presence" information can be used to control the indicator of a hard copy recorder. The position of the CRT or hard copy displays is controlled by signals related to the translation and index positions of the transducer and signals related to the oscillatory position of the transducer. In this way, both presence and position information is used to control the resultant displays or records. As a further alternative, or addition, the produced signals can be used to control a video recorder such that flaw presence and position information is recorded for subsequent video display.

As will be readily understood by those skilled in the art, the embodiment of the invention previously described depends upon specular reflections returning to the transducer generally along the same path as the incident ultrasonic pulses causing the echoes. As will also be readily appreciated, such specular reflections are reflections wherein the angle of incidence is equal to the angle of reflection. In most instances, the majority of the energy scattered by flaws form such specular reflection, and only a small amount form diffuse reflections.

Figure 11:
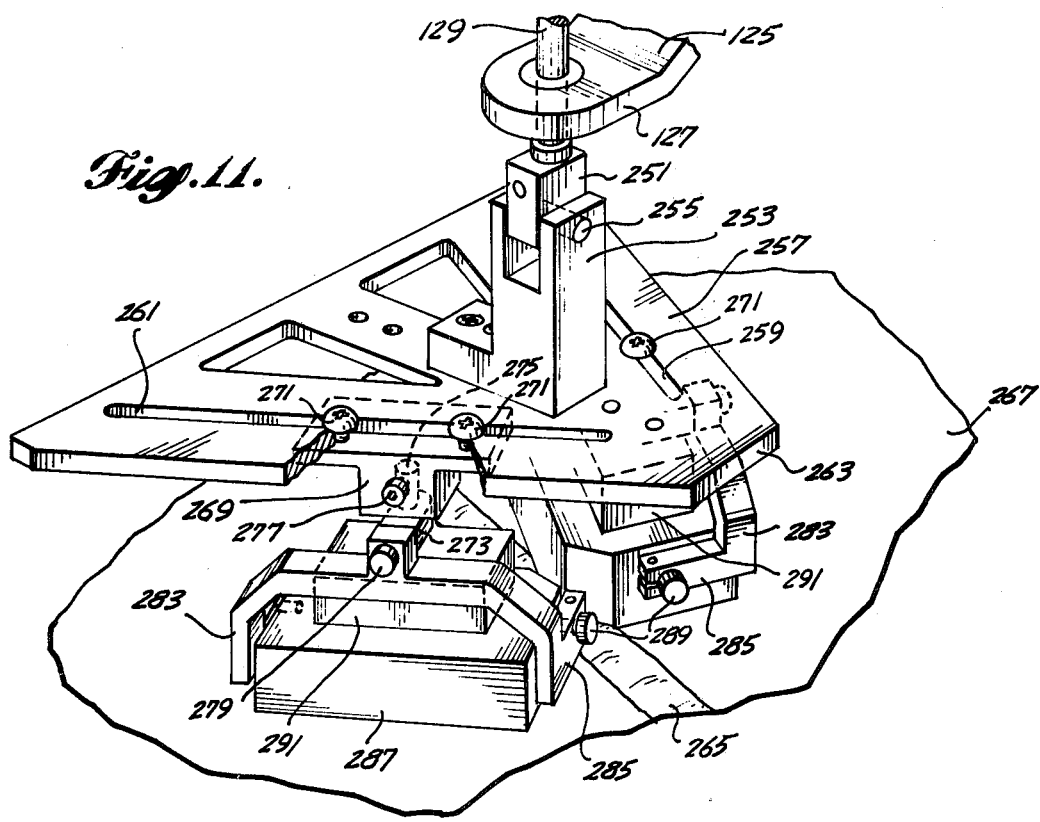

In general, an ultrasonic transducer system based on return path specular reflection phenomenon is adequate to locate flaws in strip welds. However, certain types of flaws, particularly those orthogonal to the longitudinal axis of the weld are not always readily detectable using a one transducer arrangement that depends upon return path specular reflection phenomenon. When the potential for such flaws exists, thus, it is desirable to use other types of transducer arrangements. One suitable transducer arrangement is illustrated in FIG. 11 and hereinafter described. This transducer arrangement is designed to sense specular reflections that return along a path that does not coincide with the transmission path.

As will be better understood from the following description, the transducer arrangement illustrated in FIG. 11 replaces the portion of FIG. 3 lying below the flange 127 of the lower arm 125 of the index carriage 35. Basically, this mechanism comprises the universal joint 133, the transducer 111 and its surrounding transducer support 145.

The transducer arrangement illustrated in FIG. 11 comprises a block 251 attached to the lower end of the nodder shaft 129, below the flange 127 of the lower arm 125. The block 251 is in the form of a parallelepiped and is pinned across a pair of opposing surfaces to a yoke block 253 by a pin 255. More specifically, the yoke block 253 includes an apertured end in which the block 251 lies. A pin 255 attaches the block 251 to the yoke block 253 in a rotatable manner. Thus, one axis of swiveling or rotation is provided by the coupling between the block 251 and the yoke block 253.

Mounted at the lower end of the yoke block 253, so as to lie generally parallel to the surface over which the transducer assembly is moved, is a generally triangular plate 257. First and second slots 259 and 261 are formed in the generally flat plate 257 parallel to edges that project toward a common apex. This apex 263 is flat and generally lies above the welds 265 formed in the panel 267 being inspected.

Lying beneath each of the slots 259 and 261 is a T-shaped block 269. The "head" of the T-shaped block is attached to the lower surface of the generally flat triangular plate 257 by a pair of screws 271 that pass through the related slot 259 or 261 in the generally flat plate 257. The slot/screw arrangement allows the T-shaped support elements 259 to be positioned along the longitudinal length of the slot and, after being positioned, locked in place.

Lying beneath the lower end of the T-shaped blocks 269 are swivel blocks 273. The swivel blocks 273 include upwardly projecting cylincrical shafts 275 mounted in cylindrical apertures formed in the legs of the T-shaped blocks 269. Projecting inwardly from one of the sides of the T-shaped blocks 269, are Allen-headed lock bolts 277. Thus, the swivel blocks 273 can be rotated back and forth in the cylindrical apertures in the legs of the T-shaped blocks 269 and, after being positioned for the purposes hereinafter described, locked in place by tightening of the Allen-headed lock bolts 277.

The swivel blocks 273 support shafts 279 that lie generally orthogonal to the longitudinal axis of the slots 261 and 259 formed in the plate 257. The shafts project outwardly from the center of the plate and support yokes 281. The yokes are rotatably mounted on the shafts 279 and include downwardly projecting arms 283 that terminate in inwardly (e.g., toward and beneath the plate 257) projecting flanges 285. Located between the flanges 285 of each yoke 281 is a transducer support 287 generally similar to the transducer support 145 illustrated in FIG. 3 and previously described. Pins 289 project inwardly from the outer ends of the flanges 285 and attach the transducer supports 287 to the yokes 281 in a rotatable manner. That is, the transducer supports 287 are rotatable about an axis defined by the axes of the pins 289. Mounted in the central apertures in the transducer supports 287 are transducers 291.

As will be readily appreciated from the foregoing description, the transducer assembly illustrated in FIG. 11 includes two transducers that are mounted in planes that, when appropriately adjusted, intersect. Thus, the ultrasonic beam path, either transmitting or receiving, of the transducers can be aligned. Alignment is provided by moving the transducers back and forth in the direction defined by the axes of the slots 259 and 261; and, rotating the transducers back and forth along the axes defined by the shafts 275 of the swivel blocks 273.

In addition to providing for adjustment, the transducers are free to remain in contact with the surface of the part 267 containing the weld 265 to be scanned. Such contact is accomplished by the universal joint mechanism provided. More specifically, the yoke assembly allows the transducer to rotate in two planes, one plane defined by the pins 289 affixing the outer ends of the flanges 285 to the transducer supports 287 and the other plane defined by the axis of the shaft 279 extending orthogonally outwardly from the swivel block 273. A further axis of movement is provided by the pivoting of the yoke block 253 about the block 251. These pivoting arrangements provide three axes of movement that allow the transducers to be maintained in contact with the upper surface of the panel 267.

The transducer assembly illustrated in FIG. 11 is particularly adapted for sensing specular reflections that do not return to the transmitting transducer. More specifically, when one of the transducers emits an ultrasonic beam that penetrates the panel 267 in the manner previously described with respect to FIGS. 2 and 8, specular reflections travel toward the other transducer. Thus, this transducer mechanism is particularly adapted for sensing transverse flaws, particularly when the transducers are located on opposite sides of the weld 265, as illustrated in FIG. 11. However, the transducers can be located on the same side of the weld to be inspected and still be utilized to detect similar reflections.

As with the mechanism illustrated in FIG. 3, the transducer assembly illustrated in FIG. 11 can be moved along translation and index axes similar to those illustrated in FIG. 9 and previously described. In addition, the transducer mechanism is oscillated so as to scan the weld assembly. As will be readily appreciated, index movement, in most cases, is unused. Thus, the assembly, particularly when it is inspecting a weld that passes between the transducers 291 is moved in a translation direction and oscillated.

While preferred embodiments of the invention have been illustrated and described, it will be appreciated by those skilled in the art and others that various changes can be made therein without departing from the spirit and scope of the invention. For example, as generally indicated above, the axis of rotation of the transducer may be coincident with the point where the ultrasonic beam enters the panel, or it may be between the point of entry and the weld, or the point of entry may be between the axis of rotation and the weld, as specifically illustrated. In fact, the axis of rotation may even be coincident with the portion of the weld being inspected. This latter arrangement may be the most preferable in many circumstances. Further, only one of the display portions of the subsystem illustrated and described with respect to FIG. 9 need be utilized. That is, as will be readily appreciated, the TV monitor subsystem is redundant to the storage oscilloscope display subsystem. On the other hand, in some instances, both displays may be utilized. Hence, the invention can be practiced otherwise than as specifically described herein.

The embodiments of the invention in which an exclusive property or privilege is claimed are defined as follows:

1. An ultrasonic weld inspection system for inspecting welded parts to determine the presence and location of flaws in elongate welds in said parts, said system comprising:
   (A) ultrasonic means for producing ultrasonic signals suitable for penetrating a welded part and being reflected back and forth between opposing surfaces of said part and for receiving ultrasonic signals reflected by flaws in a weld in said part being inspected, said ultrasonic means including an ultrasonic transducer for directing said produced ultrasonic signals into said part in a direction such that said signals are reflected back and forth between opposing surfaces of said part and for receiving ultrasonic signals reflected by said weld flaws, said ultrasonic transducer adapted to be ultrasonically coupled by a film of liquid to and movable over one surface of said part;
   (B) mounting means for supporting a scanning means on said one surface of said welded part along a line lying generally parallel to an elongate weld in said welded part;
   (C) scanning means mounted on said mounting means for:
      (1) supporting said ultrasonic transducer and continuously moving said ultrasonic transducer over said one surface of said part along a longitudinal axis lying generally parallel to said elongate weld in said part and about an oscillatory axis lying transverse to said one surface of said part such that said ultrasonic transducer is maintained ultrasonically coupled by said film of liquid to said one surface of said part over which said ultrasonic transducer is moved; and,
      (2) producing position signals related to the position of said transducer along said longitudinal axis and about said oscillatory axis, said scanning means including a scanning mechanism, said scanning mechanism comprising:
         (a) an elongated track mounted on said mounting means so as to lie along said longitudinal axis;
         (b) a translation carriage mounted on said elongated track;
         (c) first movement means for moving said translation carriage along said elongated track; and,
         (d) first position sensing means for sensing the position of said translation carriage along said elongated track;
         (e) transducer support means mounted on said translation carriage for supporting said transducer;
         (f) a shaft rotatably mounted on said transducer support means so as to lie along an axis orthogonal to said one surface of said welded part, the axis of said shaft forming said oscillatory axis, said transducer affixed to one end of said shaft so as to lie on the surface of a part when said mounting means supports said elongated track on said one surface of a part;
         (g) second movement means connected to said shaft for oscillating said shaft; and,
         (h) second position sensing means for sensing the oscillatory position of said shaft as said shaft is oscillated by said second movement means; and,
   (D) a display system connected to: said ultrasonic means for receiving flaw presence signals related to the receipt of said ultrasonic signals by said ultrasonic means and to said scanning means for receiving said position signals, said display system producing at least one display depicting the presence and location of flaws projected into a plane lying generally parallel to said elongate weld.

2. An ultrasonic weld inspection system as claimed in claim 1 wherein said display system produces first and second displays, said first display depicting the presence and location of flaws projected into a first plane lying parallel to said surface over which said transducer is moved and said second display depicting the presence and location of flaws projected into a second plane lying transverse to said surface and generally parallel to said elongate weld.

3. An ultrasonic weld inspection system as claimed in claim 1 wherein said transducer support means comprises:
   an index carriage for supporting said transducer;
   index support means mounted on said translation carriage for supporting said index carriage for movement in a direction orthogonal to the direction of movement of said translation carriage along said elongated track;
   third movement means for moving said index carriage along said index support means; and,
   third position sensing means for sensing the position of said index carriage along said index support means.

4. An electronic weld inspection system as claimed in claim 3 including liquid coupling means for liquid coupling said transducer to the surface of a welded part when said transducer is located on the surface of a welded part.

5. An ultrasonic weld inspection system as claimed in claim 4 wherein said ultrasonic means includes an ultrasonic pulser-receiver connected to said ultrasonic transducer for producing and applying ultrasonic pulses to said ultrasonic transducer and receiving reflected ultrasonic pulses received by said ultrasonic transducer.

6. An ultrasonic weld inspection system as claimed in claim 5 wherein said display system includes a cathode ray tube.

7. An ultrasonic weld inspection system as claimed in claim 6 wherein said cathode ray tube is operated so as to provide a TV raster-type display.

8. An ultrasonic weld inspection system as claimed in claim 6 wherein said display system produces first and second displays, said first display depicting the presence and location of flaws projected into a first plane lying parallel to said surface over which said transducer is moved and said second display depicting the presence and location of flaws projected into a second plane lying transverse to said surface and generally parallel to said elongate weld.

9. An ultrasonic weld inspection system as claimed in claim 8 wherein:
(A) said display system includes:
 (1) A sine-cosine generator connected to said third position sensing means for producing sine and cosine signals related to the oscillatory position of said transducer as sensed by said third position sensing means;
 (2) a triangular generator connected to said ultrasonic pulser-receiver for receiving a sync pulse each time an ultrasonic pulse is applied to said ultrasonic transducer by said ultrasonic pulser-receiver, said sync pulse causing said triangular generator to produce a triangular signal;
 (3) a ramp generator connected to said ultrasonic pulser-receiver for receiving a sync pulse each time said ultrasonic pulser-receiver applies an ultrasonic pulse to said ultrasonic transducer, said sync pulse causing said ramp generator to produce a ramp signal;
 (4) a first multiplier connected to said ramp generator and to said sine-cosine generator for receiving said ramp signal and said sine signal and multiplying said ramp signal by said sine signal; and,
 (5) a second multiplier connected to said ramp generator and to said sine-cosine generator for receiving said ramp signal and said cosine signal and multiplying said ramp signal by said cosine signal; and,
(B) said ultrasonic pulser-receiver is connected to control the intensity inputs of said cathode ray tube in accordance with the receipt of reflected ultrasonic signals by said ultrasonic pulser-receiver, and the outputs of said triangular generator, said first multiplier and second multiplier and, said first and second position sensors are connected to control the deflection of the beam of said cathode ray tube.

10. An ultrasonic weld inspection system as claimed in claim 9 including a multiplexer connected between the intensity and deflection inputs of said cathode ray tube and the outputs of said triangular generator, said first and second multipliers, said first and second position sensors, and the output of said ultrasonic pulser-receiver.

11. An ultrasonic weld inspection system as claimed in claim 10 including a second ultrasonic transducer; and, wherein said scanning mechanism includes mounting means for mounting said ultrasonic transducers such that the ultrasonic beam paths of said ultrasonic transducers intersect at a common point when said ultrasonic transducers are positioned on the surface of a part.

12. An electronic weld inspection system as claimed in claim 1 incluing liquid coupling means for liquid coupling said transducer to the surface of a welded part when said transducer is located on the surface of a welded part.

13. An ultrasonic weld inspection system for inspecting welded parts to determine the presence and location of flaws in elongate welds in said parts, said system comprising:
(A) ultrasonic means for producing ultrasonic pulse signals suitable for penetrating a welded part and being reflected back and forth between opposing surfaces of said part and for receiving ultrasonic signals reflected by flaws in a weld in said part being inspected, said ultrasonic means including an ultrasonic transducer for directing said produced ultrasonic pulse signals into said part in a direction such that said signals are reflected and forth between opposing surfaces of said part and for receiving ultrasonic signals reflected by said weld flaws, said ultrasonic transducer adapted to be ultrasonically coupled by a film of liquid to and movable over one surface of said part, said ultrasonic means further including an ultrasonic pulser-receiver connected to said ultrasonic transducer for applying ultrasonic pulse signals to said ultrasonic transducer and receiving reflected ultrasonic signals received by said ultrasonic transducer;
(B) mounting means for supporting a scanning means on said one surface of said welded part adjacent to one edge of an elongate weld in said welded part;
(C) scanning means mounted on said mounting means for:
 (1) supporting said ultrasonic transducer and continuously moving said ultrasonic transducer over said one surface of said part along at least one longitudinal axis lying generally parallel to said surface of said part and about an oscillatory axis lying transverse to said one surface of said part such that said ultrasonic transducer is maintained ultrasonically coupled by said film of liquid to said one surface of said part over which said ultrasonic transducer is moved; and,
 (2) producing position signals related to the position of said transducer along said at least one longitudinal axis and about said oscillatory axis; and,
(D) a display system connected to said ultrasonic means for receiving flaw presence signals related to the receipt of reflected ultrasonic signals by said ultrasonic transducer; and to said scanning means for receiving said position signals, said display system producing first and second displays, said first display depicting the presence and location of flaws projected into a first plane lying parallel to said surface over which said transducer is moved and said second display depicting the presence and location of flaws projected into a second plane lying transverse to said surface and generally parallel to said elongate weld, said display system including:
 (1) a cathode ray tube;
 (2) a sine-cosine generator connected to said scanning means for producing sine and cosine signals related to the oscillatory position of said transducer;
 (3) a triangular generator connected to said ultrasonic pulser-receiver for receiving a sync pulse each time an ultrasonic pulse signal is applied to said ultrasonic transducer by said ultrasonic pulser-receiver, said sync pulse causing said triangular generator to produce a triangular wave signal;
 (4) a ramp generator connected to said ultrasonic pulser-receiver for receiving a sync pulse each time said ultrasonic pulser-receiver applies an ultrasonic pulse signal to said ultrasonic transducer, said sync pulse causing said ramp generator to produce a ramp signal;
 (5) a first multiplier connected to said ramp generator and to said sine-cosine generator for receiving said ramp signal and said sine signal and multiplying said ramp signal by said sine signal; and, (6) a second multiplier connected to said ramp generator and to said sine-cosine generator for receiving said ramp signal and said cosine signal and multiplying said ramp signal by said cosine signal, said ultrasonic pulser-receiver also connected to control the intensity input of said cathode ray tube in accordance with the receipt of reflected ultrasonic signals by said ultrasonic pulser-receiver, and the outputs of said triangular generator, said first and second multipliers and said scanning means being connected to control the deflection of the beam of said cathode ray tube.

14. An ultrasonic weld inspection system as claimed in claim 13 wherein said cathode ray tube is operated so as to provide a TV raster-type display.

15. An ultrasonic weld inspection system as claimed in claim 13 including a multiplexer connected between the intensity and deflection inputs of said cathode ray tube and the outputs of said triangular generator, said first and second multipliers, said first and second position sensors, and the output of said ultrasonic pulser-receiver.

16. An ultrasonic weld inspection system as claimed in claim 15 including a second ultrasonic transducer; and, wherein said scanning means includes mounting means for mounting said ultrasonic transducers such that the ultrasonic beam paths of said ultrasonic transducers intersect at a common point when said ultrasonic transducers are positioned on the surface of a part.

17. An ultrasonic weld inspection system as claimed in claim 15 including recording means for receiving the signals present on the output of said multiplexer and for storing said signals.

18. An ultrasonic weld inspection system as claimed in claim 13 including recording means connected to said ultrasonic means and said scanning means for recording the information used to create said at least one display.

19. An ultrasonic weld inspection system as claimed in claim 18 wherein said recording means is a video recorder.

20. An ultrasonic weld inspection system as claimed in claim 18 wherein said recording means is a hard copy recorder.

21. A scanning mechanism for moving a transducer over a planar surface along at least one longitudinal axis lying parallel to said surface and an oscillatory axis lying transverse to said surface, and providing information relating to the position of said transducer, said scanning mechanism comprising:

an elongated track;

mounting means for mounting said elongated track on a planar surface;

a translation carriage mounted on said elongated track;

first movement means for moving said translation carriage along said elongated track;

first position sensing means for sensing the position of said translation carriage along said elongated track;

transducer support means mounted on said carriage for supporting said transducer;

a shaft rotatably affixed to said transducer support means so as lie along an axis orthogonal to the said planar surface when said support means mounts said elongated track on a planar surface, the axis of said shaft forming said oscillatory axis, said transducer affixed to one end of said shaft so as to lie on said planar surface when said support means mounts said elongated track on a planar surface;

second movement means connected to said shaft for oscillating said shaft; and, second position sensing means for sensing the oscillatory position of said shaft as said shaft is oscillated by said second movement means.

22. A scanning mechanism as claimed in claim 21 wherein said transducer support means comprises:

an index carriage for supporting said transducer;

support means mounted on said translation carriage for supporting said index carriage for movement in a direction orthogonal to the direction of movement of said translation carriage along said elongated track and orthogonal to the longitudinal axis of said shaft;

third movement means for moving said index carriage along said support means; and, third position sensing means for sensing the position of said index carriage along said support means.

23. A scanning mechanism as claimed in claim 22 wherein said transducer is an ultrasonic transducer.

24. A scanning mechanism as claimed in claim 23 including liquid coupling means for liquid coupling said ultrasonic transducer to said planar surface when said transducer is located on said planar surface.

25. A scanning mechanism as claimed in claim 23 including a second ultrasonic transducer and mounting means for mounting said ultrasonic transducers at the lower end of said shaft such that the ultrasonic beam paths of said ultrasonic transducers intersect at a common point when said ultrasonic transducers are positioned on said planar surface.

26. A scanning mechanism as claimed in claim 25 including liquid coupling means for liquid coupling said ultrasonic transducers to said planar surface when said transducers are located on said planar surface.

* * * * *

UNITED STATES PATENT AND TRADEMARK OFFICE
CERTIFICATE OF CORRECTION

PATENT NO. : 4,170,145
DATED : October 9, 1979
INVENTOR(S) : James C. Kennedy et al.

It is certified that error appears in the above-identified patent and that said Letters Patent are hereby corrected as shown below:

Column 24, line 4: "reflected and forth" is changed to --reflected back and forth--.

Signed and Sealed this

Twenty-second Day of January 1980

[SEAL]

Attest:

SIDNEY A. DIAMOND

Attesting Officer

Commissioner of Patents and Trademarks